United States Patent [19]

Wovcha et al.

[11] 4,345,034

[45] Aug. 17, 1982

[54] MYCOBACTERIUM FORTUITUM MUTANT

[75] Inventors: Merle G. Wovcha; Kevin E. Brooks, both of Kalamazoo, Mich.

[73] Assignee: The Upjohn Company, Kalamazoo, Mich.

[21] Appl. No.: 184,724

[22] Filed: Aug. 8, 1980

Related U.S. Application Data

[62] Division of Ser. No. 931,741, Aug. 7, 1978, Pat. No. 4,293,646.

[51] Int. Cl.$^3$ .......................... C12P 33/16; C12N 1/20
[52] U.S. Cl. ..................................... 435/253; 435/865
[58] Field of Search ................................ 435/55, 253

[56] References Cited

PUBLICATIONS

Lamanna et al., Basic Bacteriology, The Williams & Wilkins Co., pp. 722–727 (1965).
Metzler, Biochemistry, Academic Press Inc., pp. 945 & 946 (1977).
Mamoli et al., Ber. 70, pp. 470 & 471, 2079–2082 (1937).

*Primary Examiner*—Alvin E. Tanenholtz
*Attorney, Agent, or Firm*—Roman Saliwanchik

[57] ABSTRACT

Mutant which is used in a novel microbiological process to selectively transform steroids having 17-alkyl side chains of from 2 to 10 carbon atoms, inclusive, to yield androst-4-ene-3,17-dione (AD) as essentially the sole transformed product. AD is a valuable intermediate to make useful steroids.

1 Claim, No Drawings

MYCOBACTERIUM FORTUITUM MUTANT

This is a division of application Ser. No. 931,741, filed Aug. 7, 1978, now U.S. Pat. No. 4,293,646.

BACKGROUND OF THE INVENTION

The transformation of steroids by microorganisms has been widely studied and documented. Apparently, the earliest such work was by Mamoli and Vercellone in 1937, Ber. 70, 470 and Ber. 70, 2079. They disclosed the reduction of 17-ketosteroids to 17β-hydroxysteroids by fermenting yeast. Since then, Peterson and Murray disclosed the 11α-hydroxylation of progesterone with the fungus *Rhizopus nigricans;* see, U.S. Pat. No. 2,602,769 (1952). Kraychy et al. in U.S. Pat. No. 3,684,657 (1972) discloses the selective microbiological degradation of steroidal 17-alkyls by fermenting a steroid containing at least 8 carbons in the 17-alkyl side chain with Mycobacterium sp. NRRL B-3683 to prepare androst-4-ene-3,17-dione (AD), androst-1,4-diene-3,17-dione (ADD), and 20α-hydroxymethylpregna-1,4-dien-3-one. Marsheck et al. in U.S. Pat. No. 3,759,791 (1973) disclose the selective microbiological preparation of androst-4-ene-3,17-dione by fermenting a steroid of the cholestane or stigmastane series containing at least 8 carbons in the 17-alkyl side chain with Mycobacterium sp. NRRL B-3805, which has been characterized as *Mycobacterium vaccae.*

U.S. application Ser. No. 735,075, now abandoned, discloses a process for preparing predominantly AD using the microorganism *M. fortuitum* NRRL B-11045. Small amounts of ADD are also produced in the process. This is considered to be the best prior art process for preparing AD.

BRIEF SUMMARY OF THE INVENTION

The subject process is an improved process for preparing AD. The process uses a mutant of a microorganism selected from an adaptive mutant of the microorganism used in the best prior art process known. The mutant of the subject process, *Mycobacterium fortuitum,* NRRL B-11359, is obtained from *M. fortuitum,* NRRL B-11358, which is an adaptive mutant from *Mycobacterium fortuitum* NRRL B-11045. This latter microorganism is disclosed in abandoned U.S. application Ser. No. 735,075.

*M. fortuitum* NRRL B-11359 is characterized by its ability to selectively transform steroids having 17-alkyl side chains of from 2 to 10 carbon atoms, inclusive, and accumulate AD as essentially the sole transformed product in the fermentation beer. The best prior art process for preparing AD accumulates about four times more ADD in the fermentation beer than the subject process. A smaller amount of ADD in the fermentation beer facilitates the isolation of the desired product AD.

The mutant can be obtained by using the mutation procedures disclosed herein or other mutation procedures. The adaptive mutant of the subject invention is obtained by growing *M. fortuitum* NRRL B-11045 on a suitable medium containing 9a-OH AD. A rapid growth colony, identified as an adaptive mutant, is selected. This adaptive mutant. *M. fortuitum* NRRL B-11358, is then subjected to nitrosoguanidine (NTG) mutagenesis. The mutant of the subject invention is then selected on agar plates using a 9a-OH AD medium, as above. The desired mutant M. *fortuitum* NRRL B-11359 will not grow on a medium containing AD OR 9a-OH AD as the sole carbon source.

*Mycobacterium fortuitum,* NRRL B-11359, is used to selectively transform steroids having 17-alkyl chains of from 2 to 10 carbon atoms to AD. Examples of suitable steroid substrates are sitosterols, cholesterol, stigmasterol, campesterol, and like steroids with 17-alkyl side chains of from 2 to 10 carbon atoms, inclusive. These steroid substrates can be in either the pure or crude form.

DETAILED DESCRIPTION OF THE INVENTION

The Microorganism

The mutant of the subject invention is characterized by its ability to selectively transform steroids having 17-alkyl side chains of from 2 to 10 carbon atoms, inclusive, and accumulate AD as essentially the sole transformed product in the fermentation beer. This mutant is obtained by mutating an adaptive mutant obtained from the known AD producer *M. fortuitum* NRRL B-11045. The adaptive mutant is identified as *M. fortuitum* NRRL B-11358. The mutant obtained from this adaptive mutant, *M. fortuitum* NRRL B-11359, produces AD more efficiently than *M. fortuitum* NRRL B-11045. The production is more efficient because *M. fortuitum* NRRL B-11359 produces anywhere from about 75% to 100% less ADD, an undesired product, in the fermentation beer than does *M. fortuitum* NRRL B-11045.

*M. fortuitum* NRRL B-11358, *M. fortuitum* NRRL B-11359, and *M. fortuitum* NRRL B-11045 have been deposited in the permanent collection of the Northern Regional Research Laboratory, U.S. Department of Agriculture, Peoria, Ill., U.S.A. Subcultures of these microorganisms are available from this depository by request made thereto. It should be understood that the availability of the cultures does not constitute a license to practice the subject invention in derogation of patent rights granted with the subject instrument by governmental action.

*M. fortuitum* NRRL B-11359 is distinguishable from *M. fortuitum* NRRL B-11045 by its production of AD with lesser amounts of ADD in the fermentation beer.

*M. fortuitum* NRRL B-11045 has been distinguished from the Mycobacterium species NRRL B-3805, disclosed in U.S. Pat. No. 3,759,791, which is discussed supra. NRRL B-3805 has the general characteristics of *Mycobacterium vaccae* which is a distinctly different species than the *M. fortuitum* of the subject invention. See Bergey's Manual of Determinative Bacteriology, 8th Edition, The Williams and Wilkins Company, 1974, (on pages) 695 and 696 for a comparison of these microorganisms.

The morphology and drug sensitivities of *M. fortuitum* NRRL B-11358 and NRRL B-11359 are indistinguishable from that of *M. fortuitum,* ATCC 6842 and *M. fortuitum* NRRL B-11045. *M. fortuitum* is an acid-fast non-motile, non-spore-forming bacillus belonging to the family Mycobacteriaceae of the order Actinomycetales. According to Runyons classification, Runyon, E. H. 1959 Med. Clin. North America 43: 273, *M. fortuitum* is a nonchromogenic group IV mycobacterium, i.e., it grows rapidly at low temperatures to produce nonpigmented colonies on relatively simple media.

The mutation of *M. fortuitum* NRRL B-11358 to give *M. fortuitum* NRRL B-11359 is accomplished by the use of nitrosoguanidine. The details of the procedure are described infra.

The Transformation Process

The selective transformation of the subject invention can be effected in a growing culture of *M. fortuitum* NRRL B-11359 by either adding the selected steroid substrate to the culture during the incubation period, or incorporating it in the nutrient medium prior to inoculation. The steroid can be added singly or in combination with another steroid. The preferred, but not limiting, range of concentration of the steroid in the culture is about 0.1 to about 100 grams per liter. The culture is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, ammonium salts and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

The transformation process can range from about 72 hours to 15 days or more. The incubation temperature can range from about 25° C. to about 37° C., with 30° C. being preferred for NRRL B-11359. The contents are aerated with sterilized air and agitated to facilitate growth of the microorganism, and, thus, enhance the effectiveness of the transformation process.

Upon completion of the transformation process, as evidenced by thin layer chromatography (tlc) using silica gel plates (E. Merck, Darmstadt) and a solvent system consisting of 2:3 (by volume) ethyl acetate-cyclohexane, the desired transformed steroid is recovered by means well known in the art. For example, the fermentation (transformation) reaction mixture, including the fermentation liquor and cells, can be extracted with a water-immiscible organic solvent for steroids. Suitable solvents are dichloromethane (preferred), methylene chloride, chloroform, carbon tetrachloride, ethylene chloride, trichloroethylene, ether, amyl acetate, benzene and the like.

Alternatively, the fermentation liquor and cells can be first separated by conventional methods, e.g., filtration or centrifugation, and then separately extracted with suitable solvents. The cells can be extracted with either water-miscible or water-immiscible solvents. The fermentation liquor, freed of cells, can be extracted with water-immiscible solvents.

The extracts can be filtered through diatomaceous earth and the filtrate vacuum distilled to dryness. The resulting residue containing the desired transformed steroid then can be dissolved in a minimum of ethyl acetate-cyclohexane (20:80). This solution then can be chromatographed on silica gel. AD can be separated from the silica gel by elution with the solvent system ethyl acetate-chloroform (15:85). The compound then can be isolated as a separate entity by evaporation of the solvent and recrystallization from hexane.

The desired product of the subject invention transformation process is the known steroid intermediate AD. This compound is useful as an intermediate in the synthesis of useful steroidal hormones. For example, AD can be used to make testosterone according to processes disclosed in U.S. Pat. Nos. 2,143,453; 2,253,798; 2,264,888 and 2,356,154.

The following examples are illustrative of the process and product of the subject invention but are not to be construed as limiting. All percentages are by weight and all solvent mixture proportions are by volume unless otherwise noted.

EXAMPLE 1

Preparation of Mutant *M. fortuitum* NRRL B-11359 From *M. fortuitum* NRRL B-11358

*M. fortuitum* NRRL B-11358 is obtained by streaking *M. fortuitum* NRRL B-11045 on an agar plate medium consisting of the following ingredients:

$NH_4NO_3$: 1.0 g/liter
$K_2HPO_4$: 0.25 g/liter
$MgSO_4 \cdot 7H_2O$: 0.25 g/liter
NaCl: 0.005 g/liter
$FeSO_4 \cdot 7H_2O$: 0.001 g/liter
Distilled Water, q.s.: 1 liter The pH is adjusted to 7.0 with 1 N HCl. Agar (15 g/liter) and 9α-hydroxyandrostenedione (0.25 g/liter) are added and the medium is autoclaved for 30 minutes at 121° C. The hot medium is then poured into a sterile blender vessel, blended for several minutes, and then poured into sterile Petri plates. The plates are incubated at 28° C. for about 7 days. From the plate is selected *M. fortuitum* NRRL B-11358 which demonstrates rapid growth on the plates. *M. fortuitum* NRRL B-11358 is then subjected to mutation procedures to obtain *M. fortuitum* NRRL B-11359.

(a) Nitrosoguanidine Mutagenesis

Cells of *M. fortuitum* NRRL B-11358 are grown at 28° C. in the following sterile seed medium:

Nutrient Broth (Difco): 8 g/liter
Yeast Broth: 1 g/liter
Glycerol: 5 g/liter
TWEEN 80: 1 g/liter
Distilled Water, q.s.: 1 liter The pH is adjusted to 7.0 with 1 N NaOH prior to sterilization at 121° C. for 20 minutes.

The cells are grown to a density of about $5 \times 10^8$ per ml, pelleted by centrifugation, and then washed with an equal volume of sterile 0.1 M sodium citrate, pH 5.6. Washed cells are resuspended in the same volume of citrate buffer, a sample removed for titering (cell count), and nitrosoguanidine added to a final concentration of 50 μg/ml. The cell suspension is incubated at 37° C. in a water bath for 30 minutes, after which a sample is again removed for titering and the remainder centrifuged down and washed with an equal volume of sterile 0.1 M potassium phosphate, pH 7.0. Finally, the cells are resuspended in a sterile minimal salts medium, minus a carbon source, consisting of the following:

$NH_4NO_3$: 1.0 g/liter
$K_2HPO_4$: 0.25 g/liter
$MgSO_4 \cdot 7H_2O$: 0.25 g/liter
NaCl: 0.005 g/liter
$FeSO_4 \cdot 7H_2O$: 0.001 g/liter
Distilled Water, q.s.: 1 liter The pH is adjusted to 7.0 with 1 N HCl prior to sterilization at 121° C. for 20 minutes. The cells are then plated out to select for mutants.

(b) Selection and Isolation

The minimal salts medium described in section (a) of Example 1, but supplemented with glycerol (10 g/liter) as the sole source of carbon and energy was prepared. Agar (15 g/liter) is added, and the medium is autoclaved at 121° C. for 30 minutes and then poured into sterile Petri plates.

Mutagenized cells, as described above, are diluted and spread onto the plates.

Growth on this medium eliminates most nutritional auxotrophs produced by the mutagenesis procedure, e.g. cultures that require vitamins, growth factors, etc. in order to grow on chemically defined medium are eliminated. After incubation at 28° C. for about 7 days, the resulting colonies are replicated to test plates suitable for selecting mutants and then back onto control plates containing the glycerol-based medium. The test plates are prepared as described by Peterson, G. E., H. L. Lewis and J. R. Davis, 1962, "Preparation of uniform dispersions of cholesterol and other water-insoluble carbon sources in agar media." J. Lipid Research 3: 275-276. The minimal salts medium in these plates is as described above in section (a) of Example 1. Agar (15 g/liter) and 9α-OH AD (0.25 g/liter) are added and the resulting suspension autoclaved for 30 minutes at 121° C. The sterile, hot mixture is then poured into a sterile blender vessel, blended for several minutes, and then poured into sterile Petri plates. Foaming tends to be a problem in this procedure but can be reduced by blending when the mixture is hot and by flaming the surface of the molten agar plates. In this manner uniform dispersions of water-insoluble carbon sources are obtained which facilitates the preparation of very homogenous but opaque agar plates.

Colonies which grew on the control plates, but which showed little if any growth on test plates containing 9α-OH AD as the sole carbon source, are purified by streaking onto nutrient agar plates. After growth at 28° C., individual clones are picked from the nutrient agar plates with sterile toothpicks and retested by inoculating grided plates containing 9α-OH AD as the carbon source. Purified isolates which still exhibit a phenotype different from the parental culture are then evaluated in shake flasks.

(c) Shake Flask Evaluation

Shake flasks (500 ml) contain 100 ml of biotransformation medium consisting of the following ingredients:
Cerelose: 5.0 g/liter
$NH_4Cl$: 3.0 g/liter
$KH_2PO_4$: 0.5 g/liter
$CaCO_3$: 3.0 g/liter
$Na_3C_6H_5O_7 \cdot 2H_2O$: 3.0 g/liter
$MgSO_4 \cdot 7H_2O$: 2.0 g/liter
UREA: 0.5 g/liter
TWEEN 80*: 2.0 g/liter
Ucon**: 8.0 g/liter
*Atlas Refinery, Inc., Newark, NJ.
** Synthetic antifoam supplied by Union Carbide Chem. Co., NY, NY.
Tap $H_2O$ to 1 liter, pH adjusted to 7.0 with 1 N NaOH prior to autoclaving.

Soyflour (1 g/liter) is blended into the medium and then sitosterol (30 g/liter) is also blended into the medium. After the flasks are autoclaved for 30 minutes at 121° C., they are cooled to 28° C. and then inoculated with 10 ml of seed growth prepared as follows:

The purified isolates from part (b) are grown on agar slants at 28° C. A loop of cells taken from a slant is used to inoculate a 500-ml flask containing 100 ml of sterile seed medium consisting of the following ingredients:
Nutrient Broth (Difco): 8 g/liter
Yeast Extract: 1 g/liter
Glycerol: 5 g/liter
TWEEN 80: 1 g/liter
Distilled Water, q.s.: 1 liter The pH is adjusted to 7.0 with 1 N NaOH prior to autoclaving the flasks at 121° C. for 20 minutes. The seed flasks are incubated at 28° C. for 72 hours.

As disclosed above, 10 ml of seed growth is then used to inoculate each 500-ml flask containing 100 ml of sterile transformation medium. The flasks are then incubated at 28° C. to 30° C. on a rotary shaker and sampled at various intervals. Ten ml samples are removed and extracted by shaking with 3 volumes of methylene chloride. Portions of the extracts are analyzed by tlc using silica gel and the solvent system described above, i.e., 2:3 (by volume) ethyl acetate-cyclohexane, and by gas-liquid chromatography. Evidence of the presence of AD confirms the selective degradation of sitosterol by the mutant produced from *M. fortuitum* NRRL B-11358.

EXAMPLE 2

Transformation of Sitosterol to AD

The transformation medium used is the same as in Example 1 (c). This medium is sterilized by autoclaving 30 minutes at 121° C., whereupon it is cooled to 30° C. and then inoculated with 10 parts of a seed culture of the mutant *M. fortuitum* NRRL B-11359 prepared as described in Example 1 (c). The inoculated mixture is incubated at 30° C. for 336 hours with agitation to promote submerged growth. Following incubation, the mixture is extracted with dichloromethane. The extract is dried over anhydrous sodium sulfate and the solvent is removed by vacuum distillation. The resulting residue is dissolved in a minimum of ethyl acetate-cyclohexane (20:80). This solution is then chromatographed on silica gel. The presence of androst-4-ene-3,17-dione and a very small amount of androsta-1,4-diene-3,17-dione is shown by tlc. These compounds are separated from the silica gel by elution with the solvent system ethyl acetate-chloroform (15:85). The compounds are then isolated by evaporation of the solvent and recrystallization from hexane.

EXAMPLE 3

By substituting cholesterol for sitosterol in Example 2 there is obtained AD as essentially the sole transformed product.

EXAMPLE 4

By substituting stigmasterol for sitosterol in Example 2 there is obtained AD as essentially the sole transformed product.

EXAMPLE 5

By substituting campesterol for sitosterol in Example 2 there is obtained AD as essentially the sole transformed product.

EXAMPLE 6

By adding a combination of any of the steroids in Examples 2-5, in addition to sitosterol, or in place of sitosterol, in Example 2 there is obtained AD as essentially the sole transformed product.

We claim:
1. A biologically pure culture of mutant *Mycobacterium fortuitum* NRRL B-11359.

* * * * *